United States Patent [19]

Cava et al.

[11] 4,448,724

[45] May 15, 1984

[54] SYNTHESIS OF 4-DEMETHOXYDAUNOMYCINONE

[75] Inventors: Michael P. Cava, Wynnewood, Pa.; Domingo Dominguez, Santiago de Compostela, Spain

[73] Assignee: The Trustees of the University of Pennsylvania, Philadelphia, Pa.

[21] Appl. No.: 451,523

[22] Filed: Dec. 20, 1982

[51] Int. Cl.³ .................... C07C 50/27; C07C 87/10; C07C 50/36
[52] U.S. Cl. ............................ 260/351.5; 260/351.1; 260/365
[58] Field of Search .................. 260/376, 365, 351.1, 260/351.5

[56] References Cited

U.S. PATENT DOCUMENTS 4,070,382  1/1978  Kende et al. ............... 260/365
4,116,981  9/1978  Kende ........................ 260/376
4,154,745  5/1979  Kende et al. ............... 260/376

*Primary Examiner*—Natalie Trousof
*Assistant Examiner*—Raymond K. Covington
*Attorney, Agent, or Firm*—Marion C. Staves

[57] ABSTRACT

A synthesis of 4-demethoxydaunomycinone and its derivatives from the known compound 9-acetyl-6,11-dihydroxy-7,8,9,10-tetrahydro-5,12-naphthacenedione. 4-Demethoxydaunomycinone may be converted to 4-demethoxydaunorubicin which is an anthracycline derivative known to have antitumor activity.

1 Claim, No Drawings

SYNTHESIS OF 4-DEMETHOXYDAUNOMYCINONE

FIELD OF INVENTION

The present invention relates to a method for synthesizing 4-demethoxydaunomycinone, the aglycone of 4-demethoxy-daunorubicin, an anthracycline derivative known to have anti-tumor activity. The present invention also pertains to certain novel intermediates.

BACKGROUND OF THE INVENTION

4-Demethoxydaunorubicin is an anthracycline derivative known to have antitumor activity as reported by F. Arcamone et al in Cancer Treatment Reports, Vol. 60(7), pages 829–834 (1976). Doxorubicin and daunomycin are closely related compounds of established clinical utility. Doxorubicin hydrochloride, available from Adria Laboratories Inc. under the trade name Adriamycin ®, has been approved by the Food and Drug Administration for use in clinical research, and is one of the most powerful anticancer drugs available.

At present, doxorubicin is produced commercially from a soil fungus by a fermentation process. A suitable fermentation technique for preparing doxorubicin is described in U.S. Pat. No. 3,590,028. Such techniques are inherently expensive and limit the types of molecules that can be produced. Because of the inherent disadvantages of presently available commercial techniques for producing doxorubicin and related compounds, substantial effort has been devoted to developing processes for producing such compounds by chemical synthesis.

Several syntheses of 4-demethoxydaunomycinone have been described in the literature. See, for example, Wong et al, Can. J. Chem., Vol. 49, p. 2412 (1971); Arcamone et al, British Pat. No. 2,601,785 (1975); Suzuki et al, Tetrahedron Letters 1977 p. 2303; Kerdesky et al, J. American Chem. Soc., 100(11), p. 3635 (1978); Kende et al, Tetrahedron Letters, 1977, p. 3537; and Jackson et al, J. American Chem. Soc. 101, p. 3989 (1979). Unfortunately, all of the above syntheses suffer short-comings that limit their practical utility.

SUMMARY OF THE INVENTION

In accordance with the present invention, the known compound 9-acetyl-6,11-dihydroxy-7,8,9,10-tetrahydro-5,12-naphthacenedione, which compound may be derived from o-quinodimethane and methyl vinyl ketone by the method generally described in Kerdesky et al, J. American Chem. Soc., 100(11) p. 3635 (1978), is used as the starting material to produce 4-demethoxydaunomycinone. This latter compound may be converted to 4-demethoxydaunorubicin.

The process of the present invention for synthesizing 4-demethoxydaunomycinone involves:

(a) reacting 9-acetyl-6,11,-dihydroxy-7,8,9,10-tetrahydro-5,12-naphthacenedione(1) with acetic anhydride in a suitable organic solvent such as carbon tetrachloride in the presence of perchloric acid catalyst to form the enol-acetate(2).

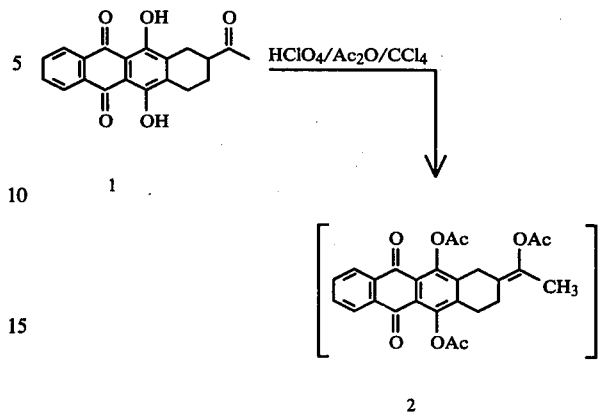

(b) epoxidation of the enol-acetate(2) with a peracid such as m-chloroperbenzoic acid.

(c) acid catalyzed rearrangement of the epoxide(3) in acetic anhydride to give the triacetate derivative(5).

(d) benzylic bromination of the triacetate derivative(5).

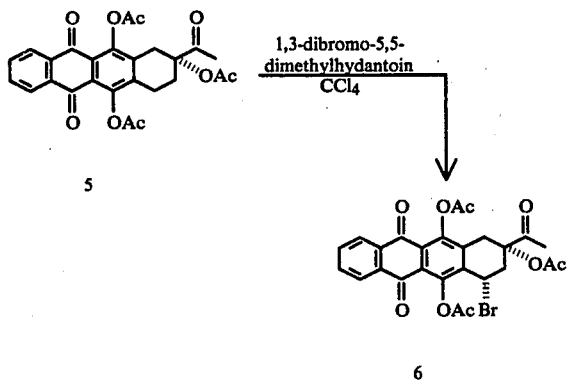

5

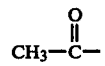

6

(e) solvolysis of the bromide derivative(6) with aqueous alkali and epimerization to form 4-demethoxydaunomycinone(7).

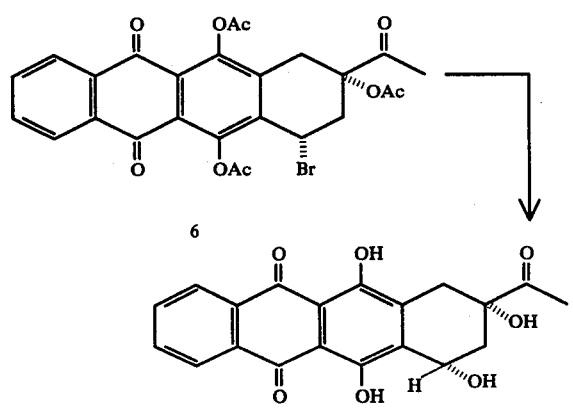

6

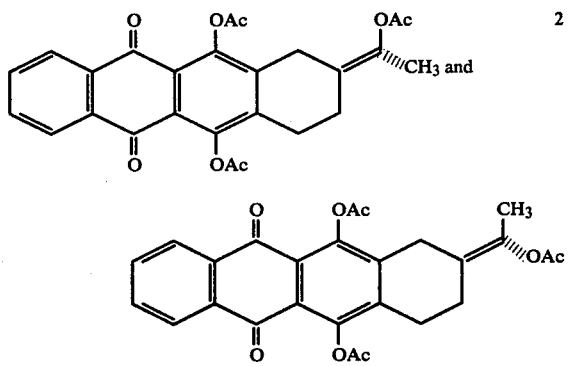

DESCRIPTION OF PREFERRED EMBODIMENTS

In the synthesis of the present invention 9-acetyl-6,11-dihydroxy-7,8,9,10-tetrahydro-5,12-naphthacenedione, a known and relatively inexpensive compound, can be used as the starting material. The starting material is first converted to the enol-acetate by a perchloric acid catalyzed reaction in an organic solvent such as a mixture of acetic anhydride and carbon tetrachloride at room temperature, i.e., a temperature in the range of from about 65°–95° F. The enol-acetate product is a mixture of both geometrical isomers.

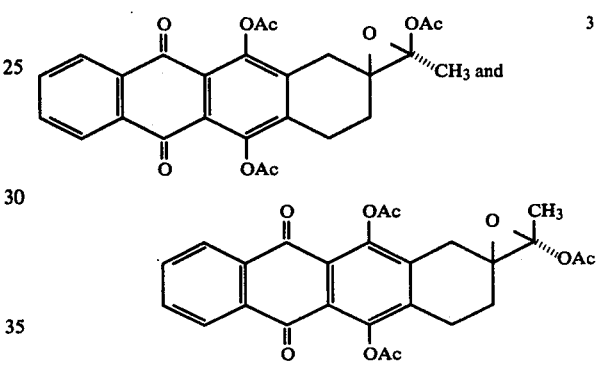

The mixed isomers do not need to be separated for purposes of this invention.

Parenthetically, in the above formulas as well as in other structural formulas appearing herein, some of the hydrogen atoms are omitted for the sake of clarity. Those skilled in the art will have no trouble comprehending the formulas to include the omitted hydrogen atoms. It should also be noted that in the above formulas, and elsewhere herein, the use of "Ac" is understood to represent the acetyl radical, i.e., $$CH_3-\overset{O}{\overset{\|}{C}}-$$

The mixed enol-acetate, dissolved in an organic solvent such as dichloromethane, is then epoxidized with a peracid such as m-chloroperbenzoic acid at room temperature, i.e., a temperature in the range of from about 65°–95° F. Again, the product is a mixture of both geometrical isomers.

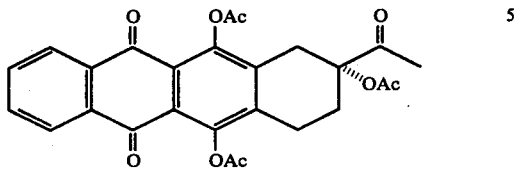

The mixed isomers do not need to be separated for purposes of this invention.

The epoxidized product is then converted to the triacetoxy derivative(5).

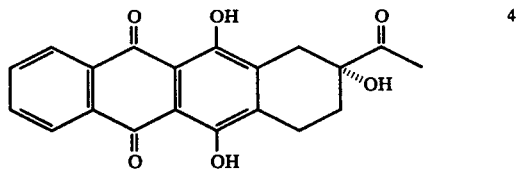

This compound can be prepared directly from the above epoxidized product(3) by acid catalyzed rearrangement of the epoxide(3) in acetic anhydride. However, the most preferred method is to first prepare the 8-acetyl-8-hydroxy-7,8,9,10-tetrahydro-6,11-dihydro-5,12-naphthacenedione(4).

by mild alkaline hydrolysis of the epoxide(3) and then acetylation of the above trihydroxy compound catalyzed by sulfuric acid. The reason that the alternative process is preferred is the ease by which impurities can be separated from the trihydroxy intermediate(4).

The triacetoxy derivative(5) is then brominated in the C-7 position using a brominating agent, such as 1,3-dibromo-5,5-dimethylhydantoin.

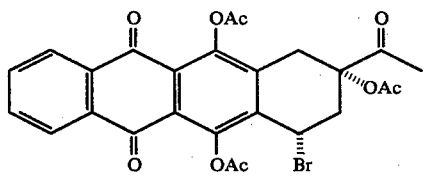

Finally, the brominated derivative(6) is solvolyzed to obtain the desired 4-demethoxydaunomycinone(7).

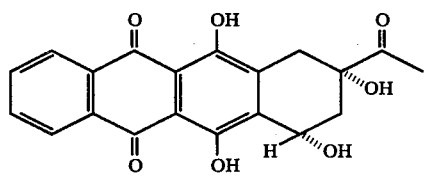

The solvolysis of the bromide derivative(6) can either be carried out directly with dilute alkali or step-wise by treating the bromide first with silver trifluoroacetate in trifluoroacetic acid followed by mild alkaline hydrolysis. The step-wise reaction is preferred since it produces higher yields of the desired product.

This invention is further illustrated by the following example in which the parts and percentages are by weight.

EXAMPLE

To a stirred suspension of 5 parts of 9-acetyl-6,11-dihydroxy-7,8,9,10-tetrahydro-5,12-naphthacenedione(1) in a mixture of 50 parts of acetic anhydride and 143 parts of carbon tetrachloride at room temperature is added 0.3 parts of perchloric acid. After 10 minutes, a homogeneous yellow solution is obtained which is stirred for 8 hours. The reaction mixture is then diluted with methylene chloride (133 parts) and poured into a cold (0°–5° C.) mixture of 266 parts of methylene chloride and 200 parts of aqueous saturated sodium bicarbonate solution. After excess solid NaHCO$_3$ is added to neutralize any acid, the organic phase is separated, dried and concentrated. To this crude enol-acetate(2) dissolved in 61 parts of methylene chloride is added 4.7 parts of m-chloroperbenzoic acid previously washed with a Na$_2$HPO$_4$ buffer. The resulting mixture is stirred at room temperature for 1 hour, diluted with methylene chloride and washed with a dilute aqueous solution of sodium sulfite. The organic phase is separated, dried and concentrated, yielding the crude epoxide(3).

The crude epoxide(3) is dissolved in a mixture of 80 parts water, 88 parts of tetrahydrofuran and 30 parts of 10% aqueous sodium hydroxide and stirred at room temperature. After 40 minutes, the reaction mixture is acidified with 12% aqueous hydrochloric acid until the color changes to dark red. It is then extracted with methylene chloride, dried and concentrated. The crude 8-acetyl-8-hydroxy-7,8,9,10-tetrahydro-6,11-dihydro-5,12-naphthacenedione(4) is chromatographed using silica gel (methylene chloride-ethyl acetate) to remove the starting ketone(1) and obtain the hydroxy ketone(4) as orange needles having a melting point of 202°–203° C.

To a suspension of 1.48 parts of the hydroxy ketone(4) in 75 parts of acetic anhydride is added a catalytic amount (0.1 part) of concentrated sulfuric acid. The resulting mixture is heated at 90° C. for 6 hours. Then the solvent is removed and the yellow residue recrystallized from methanol/methylene chloride to give the triacetoxy derivative(5).

A solution of 1.65 parts of the triacetoxy derivative(5) and 0.59 parts of 1,3-dibromo-5,5-dimethylhydantoin in 250 parts of carbon tetrachloride is refluxed under nitrogen. After 3 hours, an additional amount of brominating agent (0.1 part) is added and reflux continued for 1 hour. The solvent is removed, the residue chromatographed on silica gel (methylene chloride/ethyl acetate) and recrystallized from ethyl alcohol/methylene chloride to give pale yellow needles of the bromide derivative(6) having a melting point of 216°–217° C.

To 0.4 part of the bromide derivative(6) in 15 parts of trifluoroacetic acid is added 0.4 part of silver trifluoroacetate in 8 parts of trifluoroacetic acid and the resulting mixture is stirred at room temperature for 2 hours. After removing the solvent, the residue is taken into methylene chloride, separated from the silver salt by filtration and washed with water. The solvent is evaporated, the residue dissolved in a mixture of 13 parts of tetrahydrofuran and 15 parts of 0.5 N sodium hydroxide and is stirred under an atmosphere of nitrogen at room temperature for 2 hours. The resulting blue solution is diluted with 100 parts of water, acidified with 12% aqueous hydrochloric acid until the color changes to red, extracted with methylene chloride, dried and concentrated. The residue is purified by chromatographing on silica gel (methylene chloride/ethyl alcohol) to yield the desired 4-demethoxydaunomycinone(7), which is identified by direct comparison with the melting point, infra-red and N.M.R. spectra of an authentic sample.

What I claim and desire to protect by Letters Patent is:

1. A process for making 4-demethoxydaunomycinone comprising:

a. converting 9-acetyl-6,11-dihydroxy-7,8,9,10-tetrahydro-5,12-naphthacenedione by a perchloric acid catalyzed reaction to the enol-acetate compound having the formula

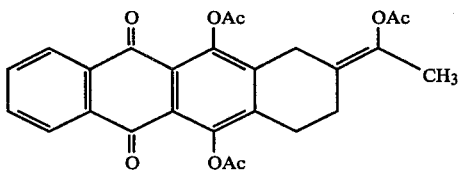

b. epoxidizing the enol-acetate compound with a peracid to produce the epoxidized compound having the formula

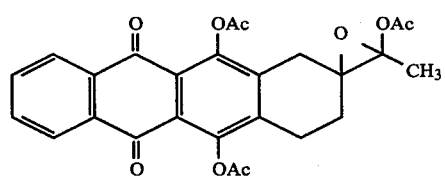

c. rearranging the epoxidized compound by alkaline hydrolysis to produce the trihydroxy compound having the formula

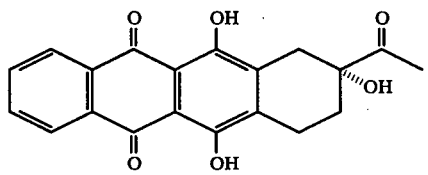

d. acetylating the trihydroxy compound to produce the triacetoxy compound having the formula

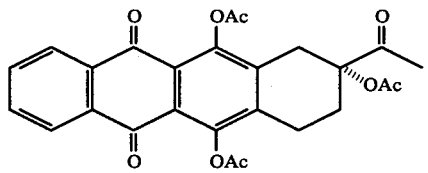

e. brominating the triacetoxy compound with a brominating agent to produce the brominated compound having the formula

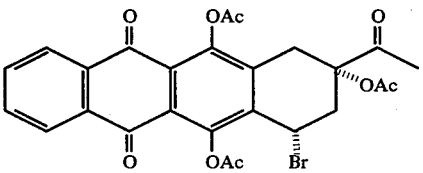

f. solvolyzing the brominated compound to produce 4-demethoxydaunomycinone having the formula

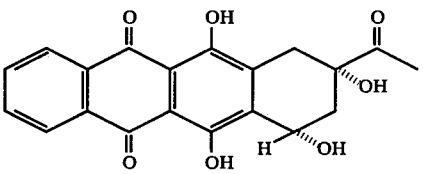

* * * * *